United States Patent [19]

Nowakowski

[11] 3,949,742

[45] Apr. 13, 1976

[54] MEDICAL DRESSING

[75] Inventor: Bogdan Nowakowski, Shelton, Conn.

[73] Assignee: Frigitronics, Inc., Shelton, Conn.

[22] Filed: Sept. 20, 1974

[21] Appl. No.: 507,744

[52] U.S. Cl. ............... 128/155; 128/156; 428/195; 428/132
[51] Int. Cl.$^2$ .................... A61F 13/00; C09J 7/02
[58] Field of Search ....... 128/155, 156, 132 D, 260; 161/109, 112, 159

[56] References Cited
UNITED STATES PATENTS

| | | | |
|---|---|---|---|
| 2,785,154 | 3/1957 | Locke | 260/114 |
| 3,434,472 | 3/1969 | Herniman et al. | 128/156 |
| 3,446,208 | 5/1969 | Fukuda | 128/156 |
| 3,520,949 | 7/1970 | Shepherd et al. | 128/156 X |
| 3,645,835 | 2/1972 | Hodgson | 128/132 D |
| 3,648,692 | 3/1972 | Wheeler | 128/156 |
| 3,663,462 | 5/1972 | Arndt et al. | 161/159 |
| 3,800,792 | 4/1974 | McKnight | 128/156 |
| 3,849,238 | 11/1974 | Gould | 161/159 |

Primary Examiner—Aldrich F. Medbery
Attorney, Agent, or Firm—Buckles and Bramblett

[57] ABSTRACT

A medical dressing is provided which is adapted to perform as a synthetic skin for the therapy and protection of skin wounds such as burns, donor sites for skin grafting, ulcers, and the like. In a preferred embodiment, the medical dressing is transparent, thin and flexible, elastomeric and conformable. The preferred medical dressing comprises a laminate of a thin layer of non-porous segmented polyurethane cohesively secured to a thin layer of thrombogenic reticulated foam.

4 Claims, 2 Drawing Figures

MEDICAL DRESSING

BACKGROUND OF THE INVENTION

Successful treatment of skin wounds such as severe burns has involved the use of fresh cadaveric skin homografts as temporary biological covering for the skin wound. The temporary covering decreases fluid and protein loss, prevents or controls infection, and enhances regeneration of new skin tissue. However, homograft skin is not readily available and has a short shelf life.

Porcine skin has been found to be a satisfactory substitute for human skin. The cost of fresh porcine heterograft is as high as $20 per square foot, and it has been demonstrated that the recipient is sometimes sensitized to porcine antigens.

Thus, there has been strong stimulus to develop suitable synthetic substitutes for fresh homograft and heterograft skin in the treatment of burns and other skin wounds. Investigations with a variety of prosthetic materials have demonstrated that none of the synthetic skin compositions developed are completely satisfactory as substitutes for homograft and heterograft skin.

Some recent U.S. patents disclose synthetic biological dressing compositions which have been developed. U.S. Pat. No. 3,526,224 describes an occlusive dressing which is a laminate of a polyurethane film and a sheet of knitted velour fabric. U.S. Pat. No. 3,648,692 describes a medical-surgical dressing which has a porous laminated construction including a facing layer of open-cell foam material and a coextensive microporous backing.

Clinical tests have shown that all of the synthetic biological dressings developed have various disadvantages as compared to homograft and heterograft skin in treatment of burns and the like.

Thus, it is a main object of the present invention to overcome the shortcomings of known synthetic dressing materials by the provision of a synthetic skin composition which is thin, flexible, elastomeric and conformable; and prevents excessive loss of body fluids, serves as a matrix for growth of fibroblasts and capillaries, and adheres securely to wound areas as a semi-permanent replacement for damaged skin.

Other objects and advantages will become apparent from the following description and accompanying drawing.

DESCRIPTION OF THE INVENTION

Figure 1:
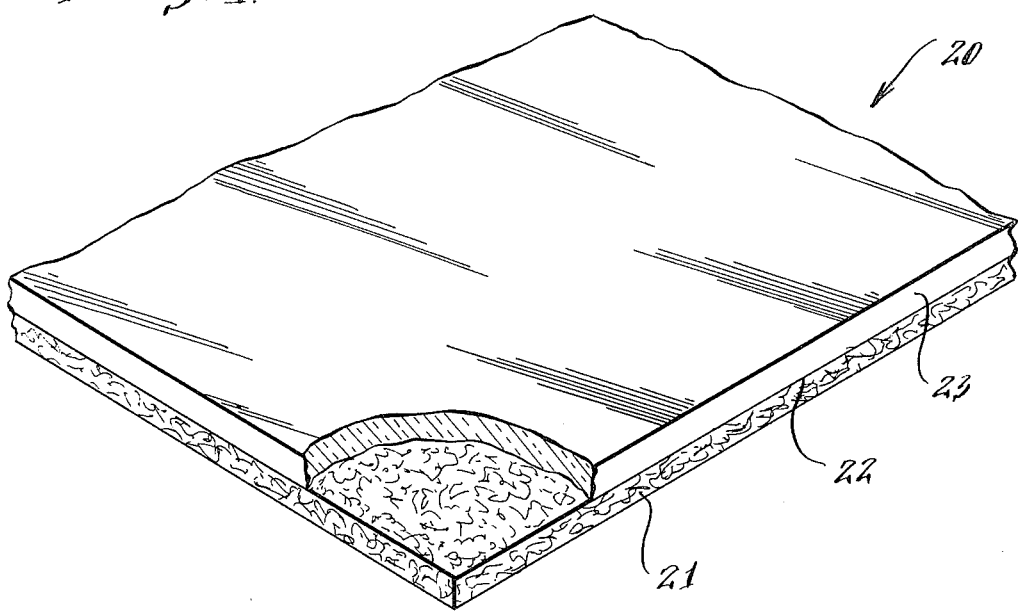
FIG. 1 is a representation of a medical dressing of the present invention comprising a laminate of a backing layer and a facing layer.
Figure 2:
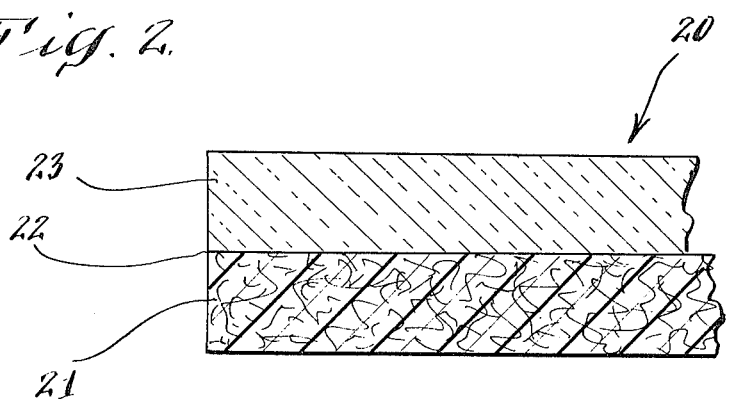
FIG. 2 is a sectional view of a medical dressing of the present invention which illustrates a backing layer cohesively secured to a thin facing layer of reticulated foam.

One or more objects of the present invention are accomplished by the provision of a medical dressing 20 for topical application to skin wounds which comprises a unitary composite of a thin facing layer 21 of thrombogenic reticulated foam cohesively secured at interface 22 to a thin non-porous elastomeric backing layer 23. Preferably, the medical dressing 20 has a thickness of between about 10 and 40 mils, and is sufficiently transparent or translucent to permit observation of the protected skin wound area beneath the medical dressing 20.

The reticulated foam facing layer must be thin and elastic on its own. The structure is composed of small sized open cells. The thickness of the foam layer is between about 8 and 60 mils, and preferably between about 10 and 40 mils. The foam cell size is between about 40 and 300 mesh, and preferably between about 100 and 200 mesh. The foam for the purposes of this invention is physiologically compatible with skin.

The elasticity of the foam cannot be utilized if it is attached to a backing layer which itself is not elastomeric, e.g., the microporous polypropylene or microporous polytetrafluoroethylene film backings disclosed in U.S. Pat. No. 3,648,692. If the foam is attached to either film, its elastomeric properties are lost. The microporous polypropylene backing is not elastomeric and the same applies to the microporous polytetrafluoroethylene backing which again is not elastomeric, although it is extensible. Extensible means here that a film (or dressing) extends with applied stress, but that it does not necessarily return to its initial length when such a stress is removed. This second type of microporous backing extends irreversibly and the elastomeric ability of the foam to return substantially to its initial length is not realized. Only if the foam is secured to a proper elastomeric backing can the resulting composite utilize the useful elastomeric potential of the foam backing.

Illustrative of a reticulated foam suitable for the practice of present invention is that described in U.S. Pat. No. 3,171,120, and that sold commercially as Scott foam, Premium Grade (Scott Paper Company). The typical reticulated foam is a crosslinked polyester-based polyurethane. The open-cell foam can be produced by treatment of closed-cell foam material with alkaline solution. An open-cell foam structure generally can be accomplished by controlled removal of a foam composition moiety with a suitable solvent.

The backing layer 23 characteristically is non-porous, elastomeric and very thin. The elasticity of the backing layer is such that stretching and flexing of the medical dressing 20 in use does not induce permanent elongation or distortion.

It is an essential feature of the backing layer that it is substantially non-porous. The backing layer is effectively an impermeable barrier. Body fluids are retained under the medical dressing 20, and bacteria are prevented from infecting the protected wound area.

By "non-porous" is meant a backing layer having an apparent density more than about 98%, and having an average pore size below about 0.01 microns. It has been found that this "non-porosity" nevertheless permits breathing in the manner of normal skin, i.e., oxygen passes through the barrier into the protected wound area, and water vapor and gases pass through the barrier at a slow rate out of the covered wound area. This selective permeability of the backing layer 23 permits aeration of the wound area, thereby preventing anaerobic infections.

It is highly preferred that the backing layer is as thin as possible, while still exhibiting strength and durability. The thickness of the backing layer is between about 0.1 and 15 mils, and preferably between about 0.2 and 10 mils. The thinness of the backing layer enhances transparency, elasticity and flexibility, and allows selective passage of oxygen and other gases or vapors.

It is believed that the passage of gases through the non-porous backing layer proceeds via a mechanism that is analogous to the movement of dissolved gas molecules through a liquid. Hence, this is not a case of gas molecules streaming through a microporous structure. It is instead a selective permeability through a barrier by diffusion of dissolved molecules.

In a preferred embodiment of the present invention the backing layer is a thin film of segmented polyurethane resins. Illustrative of suitable segmented polyurethane resins are those marketed under the tradename "Lycra" (DuPont). Segmented polyurethane resins are described in U.S. Pat. No. 2,929,804.

In a highly preferred embodiment of the present invention, the backing layer is a segmented polyurethane resin which is polyether-based rather than ester-based. The polyether-based types are much less susceptible to hydrolysis than are the ester-based types of segmented polyurethanes. The advantages of employing a polyether-based segmented polyurethane backing layer are considerable. It has been observed that a medical dressing 20 having a polyether-based segmented polyurethane backing layer 23 can perform as a semi-permanent skin protecting a burn area for a period of more than one month, without delamination or loss of adhesive to the burn area attributable to hydrolytic degradation of the medical dressing. Further, maintenance of the integrity of the backing layer 23 prevents loss of body fluids or invasion of bacteria.

with a polyamine. For example, 4,4'-diphenylmethane diisocyanate is interacted with poly(tetramethylene oxide) glycol to form a prepolymer, which is chain-extended with a mixture of ethylenediamine and 1,3-diaminocyclohexane.

The physical properties of Lycra formulation T-125 (DuPont) and other similar polyether-based segmented polyurethane resins have been published. The following table lists data relating to polyether-based segmented polyurethane resins in comparison to other commercial resins.

| Property | Method of test | Comparison of Typical Physical Properties[d] | | |
|---|---|---|---|---|
| | | Segmented Polyurethane[a] | Poly (esterurethan)[b] | Silicone rubber[c] |
| Tensile strength, psi | ASTM D412-51T | 6700 | 5840 | 1290 |
| Stress at 100% elongation, psi | ASTM D412-51T | 850 | 700 | 160 |
| Elongation at break, % | ASTM D412-51T | 750 | 540 | 560 |
| Hardness, Shore A | ASTM D676 | 75 | 88 | 50 |
| Specific gravity | — | 1.2 | 1.2 | 1.1 |

[a]Polymer T-125, E.I. du Pont de Nemours & Co., Inc.
[b]V.C. Estane 5740x1, data sheet, B.F. Goodrich Co., Cleveland, Ohio.
[c]Silastic 9711, Dow Corning Corp., Midland, Mich.
[d]J.W. Boretos et al, J. Biomed. Mater. Res, 2, 121(1968).

The next table illustrates the recovery from elongation of Lycra fiber in comparison to natural rubber.

| Elongation (%) | Permanent Set (%) | Comments |
|---|---|---|
| 100 | 3 | nat. rubber |
| 100 | 5 | 420 denier |
| 200 | 10 | 420 denier |
| 300 | 20 | 420 denier |
| 500 | 58 | 420 denier |
| 600 | 78 | 420 denier |

E.M. Hicks et al, Science, 147, 373(1965).

The next table further describes the mechanical properties of segmented polyurethane elastomer in comparison with silicone rubber.

| | Physical Properties of Segmented Polyurethane and Silicone Rubber Showing Changes After Use as Tubing in a Roller Pump at 250 rpm for Ventricular Bypass in Calves[c] | | | |
|---|---|---|---|---|
| Property | Silicone rubber[a] (control) | Silicone rubber after 2 days | Segmented polyurethane[b] (control) | Segmented Polyurethane after 6 days |
| Tensile strength, psi | 1290 | 610 | 6650 | 6450 |
| Stress at 100% elongation, psi | 160 | 95 | 857 | 852 |
| Elongation at break, % | 560 | 500 | 755 | 738 |
| Hardness, Shore Durometer A | 50 | 50 | 75 | 75 |

[a]a9711, Dow Corning Corp.
[b]Polymer T-125, E.I. DuPont Co., Inc.
[c]J.W. Boretos et al, J. Biomed. Mater. Res, 2, 121(1968).

Segmented polyurethane resin can be produced in one method by the interaction of a polyisocyanate with a poly(oxyalkylene) polyol to form a cyanato-terminated prepolymer, which in turn is chain-extended Segmented polyurethane can be sterilized by boiling water or steam. The following table summarizes the effects of autoclaving on segmented polyurethane resin.

|                              | Conditions |           |           |           |
| Property                     | A          | B         | C         | D         |
|------------------------------|------------|-----------|-----------|-----------|
| Stress at 100% elongation,   |            |           |           |           |
| psi                          | 709        | 684       | 788       | 622       |
| Standard deviation           | 28         | 19        | 87        | 22        |
| Range                        | 676–768    | 659–706   | 683–876   | 634–693   |
| Stress at failure, psi       | 6407       | 5893      | 6202      | 6049      |
| Standard deviation           | 593        | 426       | 429       | 303       |
| Range                        | 5707–7283  | 5376–6222 | 5831–6818 | 5624–6483 |
| Elongation at failure,       |            |           |           |           |
| percent                      | 715        | 740       | 672       | 758       |
| Standard deviation           | 26         | 23        | 58        | 17        |
| Range                        | 670–740    | 710–780   | 630–730   | 740–780   |

(A) 88 C, water bath for 20 min;

(B) 18.5 psi steam (125°C)

(C) 35.0 psi steam (138°C) for 20 min;
(D) 52.3 psi steam (150°C) for 20 min.
J.W. Boretos et al, J. Biomed. Mater. Res, 5, 373(1971).

The biological properties of segmented polyurethane have been investigated. It has been reported that segmented polyurethane has slow clotting tendencies, and appears rather inert toward plasma proteins and enzymes in human blood. Boretos et al in Biomed. Mater. Res. (1968 and 1971) reported that segmented polyurethane implants were barely distinguishable from control specimens. The following table lists changes in mechanical properties of in vivo specimens of segmented polyurethane.

|                                | Value[a]         |                     |                |
| Property                       | Initial (dry)    | 18 months in vivo   | Percent change |
|--------------------------------|------------------|---------------------|----------------|
| Stress at 100% elongation, psi | 586              | 550                 | 6              |
| Standard deviation             | —                | 9                   | —              |
| Range                          | —                | 540–556             | —              |
| Stress at failure, psi         | 5541             | 5274                | 5              |
| Standard deviation             | 347              | 206                 | —              |
| Range                          | 5146–5795        | 5123–5509           | —              |
| Elongation at failure, percent | 738              | 633                 | 14             |
| Standard deviation             | 10               | 6                   | —              |
| Range                          | 730–750          | 630–640             | —              |

[a]Three ring specimens (ASTM D412) were pulled at 20 in./min in a testing machine equipped with a strain-gage load cell. All specimens were cut from the same 0.040-in.-thick sheet.
J.W. Boretos et al, J. Biomed. Mater. Res, 5, 373(1971).

Segmented polyurethane resin generally dissolves to form solutions or solution-like liquids in solvents such as dimethylformamide, dimethylsulfoxide, dimethylacetamide, cyclohexanone, and the like. Ultra-thin sheets of segmented polyurethane can be cast from solution on to glass, polytetrafluoroethylene, steel or other suitable substrate. The thickness of the sheets are easily determined by controlling solution concentration or by casting a sheet in multiple layers.

The medical dressing 20 is formed by laminating coextensively a thin sheet of backing layer 23 with a thin sheet of facing layer 21. The adhesion between the sheets can be accomplished by wetting the two surfaces with a solvent before securing together, or by thermoplastic fusing, or by coating one or both contacting surfaces with an adhesive. Illustrative of suitable adhesives are Scotch Grip BM-77(3M), B MDX-4-4037 (Dow-Corning Corporation) and other adhesives disclosed in U.S. Pat. No. 3,648,692. The use of an adhesive is not preferred since it can adversely affect the flexibility, elasticity and the gas permeability of the medical dressing.

If desired, the facing layer 21 can be treated with a drug such as an antibiotic, proteolytic enzyme, topical anesthetic, and the like.

In the treatment of burns, it has been found that the medical dressing of the present invention conforms and adheres to the wound area tenaciously, and does not delaminate or slough off the wound area, and is removable from the wound area without the necessity of surgical means, and without undue discomfort to the patient. The medical dressing provides a matrix into which fibroblasts and new capillaries from the granulating bed can grow. The medical dressing is thrombogenic, immunologically inert, impervious to bacteria, and stable when stored for extended periods. The medical dressing can be sterilized by autoclaving or by treatment with a gas such as ethylene oxide.

A particularly outstanding feature of the present invention medical dressing is its ability to adhere securely to the wound area for a period of several weeks, and remain soft and elastic. It is believed that the "non-porosity" of the backing layer 23 prevents absorption of proteinacious matter and other biological solids which cause the backing layer to harden and become less elastic. Other medical dressings which have a "microporous" backing layer were tested in comparison with the invention medical dressing 20, and it was observed that the other medical dressing hardened and became less conforming in several days, and sometimes sloughed off.

The unique and long lasting elasticity and flexibility of the present invention medical dressing 20 allows the new tissue in contact with the medical dressing to form in a "stress free" condition without shrinkage and distortion of the wound area during the healing process. Further, no spaces occur under the conforming medical dressing for pockets of infection to generate. The present invention medical dressing more closely resembles a synthetic skin than any other medical dressing known and used heretofore. Also, the transparency of the preferred medical dressings of the present invention allows the viewing of the wound area through the protective covering. This is a particularly important feature in the case of severe burn wounds covering an extensive skin area, wherein it is essential to inspect the wound area frequently in order to detect and treat infection that may occur.

The following example is further illustrative of the present invention. The components of the medical dressing are presented as being typical, and various modifications can be devised in view of the foregoing disclosure within the scope of the invention.

EXAMPLE

One hundred and fifty grams of segmented polyurethane resin (DuPont, formulation T-126) and 650 ml. of dimethylacetamide are charged to a flask and stirred until the resin is dissolved.

Films are cast onto glass plates and the thickness is controlled by means of an adjustable-clearance applicator. The glass panels are placed in a vacuum oven and dried at a temperature of 50°C. The nominal thickness of the dried films is about 0.5–1.0 mil. The films exhibit excellent tear resistance when stripped from the glass plates.

A medical dressing 20 is produced by wetting the surface of the segmented polyurethane film with dimethylsulfoxide and pressing it into contact with a reticulated polyurethane foam sheet (Scottfoam). This type of polyurethane foam nominally has the following mechanical properties:

| | |
|---|---|
| Density | 2 lbs/cu. ft. |
| Thickness | 30 mils |
| Tensile Strength | 27 psi |
| Compressive Strength (at 25% of compression) | 0.5 psi |
| Ultimate Elongation | 340% |

The medical dressing so produced is an elastic composition which has excellent conformability to body contours, and is particularly suitable for covering parts of the body which flex, e.g., face, hand, foot, knee, and other flexing positions of the body.

What is claimed is:

1. A medical dressing for topical application to skin wounds which comprises a unitary composite of a thin layer of thrombogenic reticulated foam cohesively secured to a thin elastomeric backing having an apparent density more than about 98 percent and an average pore size below about 0.01 microns, wherein the said medical dressing is permeable to gases and impermeable to liquids and bacteria, and performs as a synthetic skin over skin wounds without loss of adhesiveness and flexibility.

2. A transparent medical dressing adapted for application as a flexible extensive cover for skin wounds which comprises a unitary composition of a thin layer of thrombogenic reticulated foam cohesively secured to a thin elastomeric segmented polyurethane backing having an apparent density more than about 98 percent and an average pore size below about 0.01 microns.

3. A transparent medical dressing in accordance with claim 2 wherein the reticulated foam layer is a polyurethane material between 8 and 60 mils in thickness, and has an average cell size between about 40 and 300 mesh.

4. A transparent medical dressing in accordance with claim 2 wherein the segmented polyurethane backing is a polyether-based material between about 0.01 and 15 mils in thickness.

* * * * *

UNITED STATES PATENT OFFICE
CERTIFICATE OF CORRECTION

Patent No. 3,949,742      Dated   April 13, 1976

Inventor(s)  Bogdan Nowakowski

It is certified that error appears in the above-identified patent and that said Letters Patent are hereby corrected as shown below:
Change footnote to table at bottom of Column 4 from "$1_a$9711, Dow Corning Corp." to --$^a$Silastic 9711, Dow Corning Corp.--;
Change footnote to table at top of Column 5 from "(B) 18.5 psi steam (125°C)" to --(B) 18.5 psi steam (125°C) for 20 min.--
Column 8, line 41, change "0.01" to --0.1--.

Signed and Sealed this

Twentieth Day of July 1976

[SEAL]

Attest:

RUTH C. MASON
Attesting Officer

C. MARSHALL DANN
Commissioner of Patents and Trademarks